(12) United States Patent
Murphy et al.

(10) Patent No.: US 11,197,830 B2
(45) Date of Patent: Dec. 14, 2021

(54) PHARMACEUTICAL COMPOSITION CONTAINING ACETAMINOPHEN AND IBUPROFEN

(71) Applicants: Maura Murphy, King of Prussia, PA (US); Matt Callahan, Haverford, PA (US)

(72) Inventors: Maura Murphy, King of Prussia, PA (US); Matt Callahan, Haverford, PA (US)

(73) Assignee: AFT Pharmaceuticals Limited

( * ) Notice: Subject to any disclaimer, the term of this patent is extended or adjusted under 35 U.S.C. 154(b) by 0 days.

(21) Appl. No.: 16/287,836

(22) Filed: Feb. 27, 2019

(65) Prior Publication Data

US 2020/0268673 A1 Aug. 27, 2020

(51) Int. Cl.
| | | |
|---|---|---|
| A61K 9/28 | (2006.01) | |
| A61K 31/192 | (2006.01) | |
| A61K 31/136 | (2006.01) | |
| A61K 9/00 | (2006.01) | |

(52) U.S. Cl.
CPC .......... *A61K 9/2893* (2013.01); *A61K 9/0053* (2013.01); *A61K 31/136* (2013.01); *A61K 31/192* (2013.01)

(58) Field of Classification Search
CPC .. A61K 9/2893; A61K 9/0053; A61K 31/192; A61K 31/136; A61K 9/2866; A61K 9/145; A61K 9/146; A61K 9/2018; A61P 29/00

See application file for complete search history.

(56) References Cited

U.S. PATENT DOCUMENTS

| | | | |
|---|---|---|---|
| 5,260,337 A | 11/1993 | Sims et al. | |
| 5,409,709 A * | 4/1995 | Ozawa | A61K 9/209 424/464 |
| 5,854,226 A | 12/1998 | Penkler et al. | |
| 6,440,983 B1 | 8/2002 | Frank-Kollman | |
| 2008/0200549 A1 | 8/2008 | Atkinson | |
| 2008/0275125 A1 | 11/2008 | Atkinson | |
| 2009/0264530 A1 | 10/2009 | Nickell | |
| 2010/0286100 A1 * | 11/2010 | First | A61K 9/143 514/165 |
| 2010/0288665 A1 * | 11/2010 | Lomaga | A61K 31/137 206/438 |
| 2011/0166234 A1 | 7/2011 | Atkinson | |
| 2011/0275718 A1 | 11/2011 | Atkinson | |

FOREIGN PATENT DOCUMENTS

| | | |
|---|---|---|
| AU | 605538 | 7/1989 |
| CA | 1336687 | 8/1995 |
| JP | 11158066 | 6/1999 |
| JP | 5148139 | 7/2012 |
| KR | 10-2006-0072839 | 6/2006 |
| WO | WO 2006/00449 | 1/2006 |
| WO | WO2007/034135 | 3/2007 |
| WO | WO2008079818 | 7/2008 |
| WO | WO2010/121321 | 10/2010 |
| WO | WO 2010/121328 | 10/2010 |
| WO | WO2010/132095 | 11/2010 |
| WO | WO2012005605 | 1/2012 |

OTHER PUBLICATIONS

Moore et al. "Effects of food on pharmacokinetics of immediate release oral formulations of aspirin, dipyrone, ,paracetamol and NSAIDs—a systematic review," (2015) *British Journal of Clinical Pharmacology* 80:381-388.
Moore et al., "Faster, higher, stronger? Evidence for formulation and efficacy for ibuprofen in acute pain," (2014) *Pain* 155:14-21.
AE Pickering et al., "Double-blind, placebo-controlled analgesic study of ibuprofen or rofecoxib in combination with paracetamol for tonsillectomy in children," British Journal of Anaesthesia; 2002; 88(1):72-7.
JJ Homer et al., "Audit of pain management at home following tonsillectomy in children," The Journal of Laryngology & Otology, Mar. 2001, vol. 115:205-208.
Rainsford et al., "Ibuprofen and Paracetamol: Relative Safety in Non-Perscription Dosages," J. Pharm. Pharmacol, vol. 49:345-376 (1997).
Mehlisch, D. et al., "Comparison of the Analgesic Efficacy of Concurrent Ibuprofen and Paracetamol with Ibuprofen or Paracetamol Alone in the Management of Moderate to Severe Acute Postoperative Dental Pain in Adolescents and Adults: A Randomized, Double-Blind, Placebo-Controlled, Parallel-Group, Single-Dose, Two-Center, Modified Factorial Study," Clinical Therapeutics, vol. 32, No. 5:882-895 (2010).
Merry, A. et al., "Combined Acetaminophen and Ibuprofen for Pain Relief after Oral Surgery in Adults: a Randomized Controlled Trial," British Journal of Anaesthesia, vol. 104, No. 1:80-88 (2010).
Moore, R. et al., "Validating Speed of Onset as a Key Component of Good Analgesic Response in Acute Pain," European Journal of Pain, No. 19:187-192 (2015).
Craen et al., "Analgesic efficacy and safety of paracetamol-codeine combinations versus paracetamol alone: a systematic review," BMJ, 313:321-325, 1996.
Dahl et al., "Ibuprofen vs. acetaminophen vs. ibuprofen and acetaminophen after arthroscopically assisted anterior cruciate ligament reconstruction," European Journal of Anaesthesiology, 21(6):471-475, 2004.
Doherty et al., "A randomised controlled trial of ibuprofen, paracetamol or a combination tablet of ibuprofen/paracetamol in community-derived people with knee pain," Annals of the Rheumatic Diseases, 70(9): 1534-1541, 2011.
Merry et al., "Randomized comparison between the combination of acetaminophen and ibuprofen and each constituent alone for analgesia following tonsillectomy in children," Canadian Journal of Anaesthesia, 60(12): 1180-1189, 2013.
http://medical-dictionary.thefreedictionary.com/unit+dose, accessed on May 17, 2015.

(Continued)

*Primary Examiner* — Quanglong N Truong
(74) *Attorney, Agent, or Firm* — Fish & Richardson P.C.

(57) ABSTRACT

Solid oral dosage forms containing 325 mg of acetaminophen and 97.5 mg of ibuprofen or 500 mg of acetaminophen and 150 mg of ibuprofen, wherein the ibuprofen has a [D50] between 1 and 9 μm, are described.

21 Claims, No Drawings

(56) References Cited

OTHER PUBLICATIONS

Antman et al., Use of Nonsteroidal Antiinflammatory Drugs: An Update for Clinicians: A Scientific Statement from the American Heart Association; Circulation 2007, published Feb. 26, 2007:1634-1642.

Hinz et al., Acetaminophen (paracetamol) is a selective cyclooxygenase-2 inhibitor in man, The FASEB Journal, pp. 383-390.

Bookstaver et al., "Intravenous ibuprofen: the first injectable product for the treatment of pain and fever," Journal of Pain Research, 2010:3:67-79, Published online May 25, 2010.

Bhandari et al., "Co-Amorphization of Ibuprofen by Paracetamol for Improved Processability, Solubility, and In vitro Dissolution," Acta Chim, Slov. 2018, 65, 492-501.

\* cited by examiner

PHARMACEUTICAL COMPOSITION CONTAINING ACETAMINOPHEN AND IBUPROFEN

BACKGROUND

For various non-steroidal anti-inflammatory drugs (NSAIDs) there is evidence that high, early plasma concentrations result in better early pain relief, better overall pain relief, longer lasting pain relief and lower rates of remedication. (Moore et al. (2015) *British Journal of Clinical Pharmacology* 80:381). For ibuprofen, more rapid absorption can result in earlier and higher maximum plasma concentrations and this results in earlier onset of analgesia and better overall and longer lasting analgesia in dental pain models. The effect of fast acting formulations can be significant. In one study 200 mg of a fast acting formulation, a ibuprofen salt produced the same or better analgesia as 400 mg ibuprofen acid, and with a reduced requirement for additional analgesic use (Moore et al. (2014) Pain 155:14). It is possible to alter the pharmacokinetics of ibuprofen by reducing the particle size to below 1000 nm (WO 2010/121328)

SUMMARY

Described herein is a solid oral unit dosage pharmaceutical composition containing acetaminophen (325 mg) and ibuprofen (97.5 mg) having a higher maximum plasma concentration for ibuprofen compared to Maxigesic (325). Also described is a solid oral unit dosage pharmaceutical composition containing acetaminophen (500 mg) and ibuprofen (150 mg). These dosage forms are referred to as Rapid Maxigesic 325 and Rapid Maxigesic 500, respectively. This disclosure features these pharmaceutical compositions as well as methods for producing and using such compositions.

The solid oral dosage forms described herein include ibuprofen (free acid) that is particularly rapidly dissolving in vitro. The impact of increased in vitro dissolution rates on pharmacokinetic parameters is highly variable. In the case of the present dosage forms, the rapidly dissolving ibuprofen results in a product with meaningfully higher Cmax for ibuprofen. Significantly, the ibuprofen in the present dosage forms has a particle size that is larger than 1,000 nm.

Described herein is a solid oral dosage form comprising 325 mg of acetaminophen and 97.5 mg of ibuprofen or 500 mg of acetaminophen and 150 mg of ibuprofen, wherein the ibuprofen has a [D50] between 1 and 9 μm.

In various embodiments: the ibuprofen has a [D10] between 1 and 3 μm; the ibuprofen has a [D90] between 3 and 16 μm; the ibuprofen has a [D50] between 2 and 8 μm, a [D10] between 1 and 3 μm and a [D90] between 4 and 16 μm; the dissolution rate of ibuprofen in the solid oral dosage form is such that, when tested using USP Apparatus II (paddles) set to rotation speed of 50 rpm in 900 mL of 50 mM pH 5.8 phosphate buffer at 37° C., wherein 80% or more (e.g., at least 85% to 95% or 95% to 100%) of the ibuprofen dissolves in 15 minutes or less; the dosage form is a tablet (e.g., a coated tablet); the [D90] to [D50] ratio is between 4:1 and 1.5:1; the [D90] to [D50] ratio is between 3:1 and 1.5:1; the [D50] to [D10] ratio is between 4:1 and 1.5:1; and the [D50] to [D10] ratio is between 3:1 and 1.5:1.

In some cases, the dosage form is prepared by a process comprising jet milling a composition comprising 21-23% wt/wt ibuprofen and 73-75% wt/wt acetaminophen. In some cases, the composition subjected to jet milling further comprises a surfactant (e.g., sodium lauryl sulfate).

Also described is a method for treating pain (e.g., mild to moderate acute pain) comprising administering a dose of 1, 2 or 3 units of the solid oral dosage form comprising 325 mg of acetaminophen and 97.5 mg of ibuprofen. In some cases, the administration is 1, 2, 3 or 4 times daily.

Also described is a method for treating pain (e.g., mild to moderate acute pain) comprising administering a dose of 1 or 2 units of the solid oral dosage form comprising 500 mg of acetaminophen and 150 mg of ibuprofen. In some cases, the administration is 1, 2, 3 or 4 times daily.

Also described is a method for preparing a pharmaceutical composition, comprising jet milling a composition comprising acetaminophen, ibuprofen and a surfactant (e.g. sodium lauryl sulfate), wherein the ratio of acetaminophen to ibuprofen is 3:1 (w/w), under conditions and for a time to reduce the particle size of the ibuprofen to a median particle size, on a volume average basis between 2 and 8 μm.

Also describes is a method for preparing a pharmaceutical composition, comprising jet milling a composition comprising acetaminophen, ibuprofen and a surfactant (e.g. sodium lauryl sulfate), wherein the ratio of acetaminophen to ibuprofen is 3:1 (w/w), under conditions and for a time to achieve a median bulk particle size between 4 and 15 μm.

In some cases: the [D90] of the ibuprofen in Rapid Maxigesic 325 and Rapid Maxigesic 500 is greater than 2 μm (e.g., greater than 3, 4, 5 6, 7, 8, 9, 10, 11 or 12 μm) and less than one of: 18 μm, 17 μm 16 μm; 14 μm, and 13 μm (preferably 3-17 μm 3-16 μm or 4-15 μm); the [D50] of the ibuprofen greater than 1 μm, 1.5 μm, 2 μm, 2.5 μm, 3 μm, 3.5 μm, 4 μm, 4.5 μm, 5 μm, 5.5 μm, 6 μm), but less than 12 μm, 10 μm, 9 μm, or 8 μm (preferably 1-11 μm, 1-10 μm, 2-10 μm, 2-9 μm); the [D10] of the ibuprofen is less than 7 μm (e.g., 6.5, 6, 5.5, 5, 4.5, 4, 3.5, 3, 2.5, 2, or 1.5 μm), but greater than 100 nm; the ratio of [D90] to [D50] is between 4:1 and 2:1; and the ratio of [D50] to [D10] is between 3:1 and 1.5:1 (all measurements on a volume average basis).

Also described herein is a method for treating pain, e.g., mild to moderate acute pain, comprising administering to a patient in need thereof a therapeutically effective dose (acetaminophen 975 mg+ibuprofen 292.5 mg) of the Rapid Maxigesic 325 unit dosage form (acetaminophen 325 mg+ibuprofen 97.5 mg/unit dose) up to 4 times a day (acetaminophen 3900 mg+ibuprofen 1170 mg/day).

Also described herein is a method for treating pain, e.g., mild to moderate acute pain, comprising administering to a patient in need thereof a therapeutically effective dose (acetaminophen 1000 mg+ibuprofen 300 mg) of the Rapid Maxigesic 500 unit dosage form (acetaminophen 500 mg+ibuprofen 150 mg/unit dose) up to 4 times a day (acetaminophen 4000 mg+ibuprofen 1200 mg/day).

Additional dosage regimes for Rapid Maxigesic 325 include: 1 unit dose given 1, 2, 3 or 4 times daily; 2 unit doses given 1, 2, 3 or 4 times daily; and 3 unit doses given 1, 2, 3 or 4 times daily. Additional dosage regimes for Rapid Maxigesic 500 include: 1 unit dose given 1, 2, 3 or 4 times daily and 2 unit doses given 1, 2, 3 or 4 times daily.

The dissolution rate of the ibuprofen in a coated tablet containing 97.5 mg of ibuprofen is such that when tested in 900 ml of pH 5.8 phosphate buffer (50 mM) using USP Apparatus II at 50 rpm and 37° C., is such that at least 75%, 80% or 85% ibuprofen dissolves in 15 min or less (e.g., 14 min or less, 13 min or less, e.g., 85% can dissolve in 15 min). For example, at least 85% can dissolve in 12-19 minutes.

The dissolution rate the ibuprofen in a coated tablet containing 150 mg of ibuprofen is such that when tested in 900 ml of pH 5.8 phosphate buffer (50 mM) using USP Apparatus II at 50 rpm and 37° C., is such that at least 75%, 80% or 85% ibuprofen dissolves in 15 min or less (e.g., 14 min or less, 13 min or less, e.g., 85% can dissolve in 15 min). For example, at least 85% can dissolve in 12-19 minutes.

The dosage form can include various excipients. For example, the dosage form can include one or more of: a diluent, lubricant, disintegrant, binder and wetting agent. For example, the dosage form can include one or more of: magnesium stearate, povidone, lactose, microcrystalline cellulose pregelatinized starch, hypromellose, sodium starch glycolate, sodium starch fumarate, sodium lauryl sulfate, and croscarmellose sodium. The tablet can be uncoated or, preferably, coated with a suitable coating agent.

The dry milling apparatus used is preferably a jet mill (e.g., a spiral jet mill).

In another aspect, the disclosure comprises a method for manufacturing a pharmaceutical composition as described herein comprising the step of combining a composition comprising ibuprofen and acetaminophen prepared by a method described herein or a composition as described herein, together with one of a diluent, lubricant, excipient, disintegrant, and wetting agent, to produce a pharmaceutically acceptable solid dosage form.

The disclosure described herein may include one or more ranges of values (e.g. size, concentration etc.). A range of values will be understood to include all values within the range, including the values defining the range, and values adjacent to the range that lead to the same or substantially the same outcome as the values immediately adjacent to that value which defines the boundary to the range.

Throughout this specification, unless the context requires otherwise, the word "comprise" or variations, such as "comprises" or "comprising" will be understood to imply the inclusion of a stated integer, or group of integers, but not the exclusion of any other integers or group of integers. It is also noted that in this disclosure, and particularly in the claims and/or paragraphs, terms such as "comprises", "comprised", "comprising" and the like can have the meaning attributed to it in US Patent law; e.g., they can mean "includes", "included", "including", and the like.

"Therapeutically effective amount" as used herein with respect to methods of treatment and in particular drug dosage, shall mean that dosage that provides the specific pharmacological response for which the drug is administered in a significant number of subjects in need of such treatment. It is emphasized that "therapeutically effective amount," administered to a particular subject in a particular instance will not always be effective in treating the diseases described herein, even though such dosage is deemed a "therapeutically effective amount" by those skilled in the art. It is to be further understood that drug dosages are, in particular instances, measured as oral dosages, or with reference to drug concentrations as measured in blood.

Those skilled in the art will appreciate that the disclosure described herein is susceptible to variations and modifications other than those specifically described. It is to be understood that the disclosure includes all such variations and modifications. The disclosure also includes all of the steps, features, compositions and materials referred to or indicated in the specification, individually or collectively and any and all combinations or any two or more of the steps or features.

The present disclosure is not to be limited in scope by the specific embodiments described herein, which are intended for the purpose of exemplification only. Functionally equivalent products, compositions and methods are clearly within the scope of the disclosure as described herein.

Other aspects and advantages of the disclosure will become apparent to those skilled in the art from a review of the ensuing description.

DETAILED DESCRIPTION

Described herein are various rapid release, solid oral dosage forms containing 325 mg acetaminophen and 97.5 mg of ibuprofen with higher maximum plasma concentration of ibuprofen compared to a dosage form referred to as Maxigesic 325. Also described below are various rapid release, solid oral dosage forms containing 500 mg acetaminophen and 150 mg of ibuprofen with higher plasma concentration of ibuprofen compared to a dosage form referred to a Maxigesic 500.

Maxigesic 325 tablets contain acetaminophen (325 mg) and ibuprofen (97.5 mg) and Maxigesic 500 tablets contain acetaminophen (500 mg) and ibuprofen (150 mg). Both are given in single doses of up to three tablets for the lower strength and up to two tablets for the higher strength. The amount of acetaminophen delivered in a single dose is similar in both cases being either up to three tablets of Maxigesic 325: acetaminophen 975 mg and ibuprofen 292.5 mg or two tablets Maxigesic 500: acetaminophen 1000 mg and ibuprofen 300 mg.

Particle Size

For measurements made using a laser diffraction the term "median particle size" is defined as the median particle diameter as determined on an equivalent spherical particle volume basis. Where the term median is used, it is understood to describe the particle size that divides the population in half such that 50% of the population on a volume basis is greater than or less than this size. The median particle size is written as: [$D_{50}$] or $D_{[50]}$ or [D50], D50, D(0.50) or D[0.5] or similar. As used herein [$D_{50}$] or $D_{[50]}$ or [D50], D50, D(0.50) or D[0.5] or similar shall be taken to mean median particle size.

The term "Dx of the particle size distribution" refers to the xth percentile of the distribution on an equivalent spherical particle volume basis; thus, D90 refers to the $90^{th}$ percentile, D95 refers to the $95^{th}$ percentile, and so forth. Taking D90 as an example this can often be written as, [$D_{90}$] or $D_{[90]}$ or [D90], D(0.90) or D[0.9] or similar. With respect to the median particle size and Dx an upper case D or lowercase d are interchangeable and have the same meaning.

The term "D(3,2)" is referred to as the area-weighted mean size or the Sauter diameter; the term "D(4,3)" is referred to as the volume-weighted mean size. Detailed descriptions of how these values are calculated are known in the art and can be found in, for example, ISO 9276-2:2014 (E).

For many of the materials subject to the methods of this disclosure the particle size can be easily measured. Where the active material has poor water solubility and the matrix it is milled in has good water solubility the powder can simply be dispersed in an aqueous solvent. In this scenario the matrix dissolves leaving the active material dispersed in the solvent. This size of the particles in the suspension can then be measured by laser light diffraction.

Medicaments

The medicaments of the present disclosure may include the pharmaceutically acceptable material, optionally together with a grinding matrix or at least a portion of the grinding matrix, combined with one or more pharmaceutically acceptable carriers, as well as other agents commonly used in the preparation of pharmaceutically acceptable compositions.

As used herein "pharmaceutically acceptable carrier" includes any and all solvents, dispersion media, coatings, antibacterial and antifungal agents, isotonic and absorption delaying agents, and the like that are physiologically compatible.

Pharmaceutical acceptable carriers according to the disclosure may include one or more of the following examples:
(1) surfactants and polymers including, but not limited to polyethylene glycol (PEG), polyvinylpyrrolidone (PVP), sodium lauryl sulfate, polyvinylalcohol, crospovidone, polyvinylpyrrolidone-polyvinylacrylate copolymer, cellulose derivatives, hydroxypropylmethyl cellulose, hydroxypropyl cellulose, carboxymethylethyl cellulose, hydroxypropyllmethyl cellulose phthalate, polyacrylates and polymethacrylates, urea, sugars, polyols, and their polymers, emulsifiers, sugar gum, starch, organic acids and their salts, vinyl pyrrolidone and vinyl acetate
(2) binding agents such as various celluloses and cross-linked polyvinylpyrrolidone, microcrystalline cellulose, povidone; and or
(3) filling agents such as lactose monohydrate, lactose anhydrous, microcrystalline cellulose and various starches; and or
(4) lubricating agents such as colloidal silicon dioxide, talc, stearic acid, magnesium stearate, calcium stearate, sodium stearyl fumarate; and or
(5) sweeteners such as any natural or artificial sweetener including sucrose, xylitol, sodium saccharin, cyclamate, aspartame, and acesulfame K; and or
(6) flavoring agents; and or
(7) preservatives such as potassium sorbate, methylparaben, propylparaben, benzoic acid and its salts, other esters of parahydroxybenzoic acid such as butylparaben, alcohols such as ethyl or benzyl alcohol, phenolic chemicals such as phenol, or quarternary compounds such as benzalkonium chloride; and or
(8) buffers; and or
(9) Diluents such as pharmaceutically acceptable inert fillers, such as microcrystalline cellulose, lactose, dibasic calcium phosphate, saccharides, and/or mixtures of any of the foregoing; and or
(10) wetting agents such as docusate sodium, sodium lauryl sulfate, phospholipids, poloxamer, polysorbate 80, sorbitan esters, tricaprylin, glyceryl monooleate, myristyl alcohol and mixtures thereof; and or
(11) disintegrants; such as croscarmellose sodium, crospovidone, sodium starch glycolate, and or
(12) effervescent agents such as effervescent couples such as an organic acid (e.g., citric, tartaric, malic, fumaric, adipic, succinic, and alginic acids and anhydrides and acid salts), or a carbonate (e.g. sodium carbonate, potassium carbonate, magnesium carbonate, sodium glycine carbonate, L-lysine carbonate, and arginine carbonate) or bicarbonate (e.g. sodium bicarbonate or potassium bicarbonate); and or
(13) other pharmaceutically acceptable excipients.

Example 1: Attritor Milling and Jet Milling Improve Dissolution of Ibuprofen

Attritor milling of an active pharmaceutical ingredient (API), whether dry or wet, most often takes place in the presence of a milling matrix, i.e., one or more non-active ingredients that can assist in particle size reduction of the API. For example, in a dry milling process, the API can be milled in the presence of lactose or another suitable excipient. Such milling can be used to reduce the median particle size to less than 1,000 nm. Due to the high drug load desired for the present dosage form, the acetaminophen was used as the milling matrix for the attritor milling studies described below.

Ibuprofen, acetaminophen and sodium lauryl sulfate (SLS) were milled in an attritor mill using the conditions described in Table 1.

TABLE 1

Milling Conditions for Attritor Mill

| Formula | | | |
|---|---|---|---|
| Ingredient | % w/w | Processing parameters | |
| Ibuprofen | 22.5% | Atritor Mill | 0.5 gallon, 1 S |
| Acetaminophen (APAP) | 75.5% | Media:powder ratio | 35:1 |
| Sodium Lauryl Sulfate (SLS) | 2.0% | Milling speed | 500 rpm |
| Total | 100% | Milling time yield | 40 min 51.8% |

The attritor milling (Table 1) of a mixture of acetaminophen, ibuprofen and sodium lauryl sulfate at a 200 g scale was successful in that the median particle size of the ibuprofen was reduced to the submicron range (Table 2). Moreover, the dissolution rate of the ibuprofen in the milled material, either attritor milled or jet milled, was faster than that of the unmilled API (Table 3). However, the attritor milling yield was relatively low due to caking of the milled material.

Co-jet milling was investigated as an alternative approach that might increase yield and improve scale. The formula in Table 1 was processed in a 4" jet mill with 100 prig pressure. As shown in Table 2, the ibuprofen within the co-jet milled formulation (acetaminophen/ibuprofen/SLS) was larger in size compared to the ibuprofen produced by attritor milling.

TABLE 2

Particle size of ibuprofen

| | Dv10 (μm) | Dv50 (μm) | Dv90 (μm) |
|---|---|---|---|
| Ibuprofen (starting material) | 24.2 | 51.3 | 94.5 |
| Attritor-milled intermediate | 0.282 | 0.617 | 2.05 |
| Co-Jet-milled intermediate | 1.63 | 2.73 | 4.44 |

Both milled formulations had substantially faster ibuprofen dissolution compared to the unmilled formulation, demonstrating that particle size reduction improved the ibuprofen dissolution rate. However, while the attritor milled material had much smaller particle size for ibuprofen than the co-jet milled material, the dissolution rates of ibuprofen for both milled materials (Table 3) were similar. This suggests that the co-jet milled material could overcome the dissolution rate limited solubility of ibuprofen, despite the fact that the median particle size was greater than 1,000 nm.

TABLE 3

Ibuprofen dissolution rate in acetaminophen/ibuprofen powder formulations

| Time (min) | Prior to miling | | Attritor milled | | Co-Jet-milled | |
|---|---|---|---|---|---|---|
| | % ibuprofen Dissolved | % RSD n = 3 | % ibuprofen Dissolved | % RSD n = 3 | % ibuprofen Dissolved | % RSD n = 3 |
| 2 | 34.4 | 4.4 | 82.5 | 5.5 | 96.0 | 1.3 |
| 5 | 49.2 | 6.6 | 94.9 | 1.7 | 103.0 | 0.4 |
| 10 | 62.3 | 7.4 | 100.1 | 0.5 | 103.5 | 0.4 |
| 15 | 68.3 | 9.6 | 103.5 | 0.8 | 104.7 | 1.2 |
| 30 | 73.1 | 8.8 | 103.1 | 0.2 | 105.6 | 0.3 |
| 45 | 75.8 | 6.7 | 103.3 | 0.9 | 104.0 | 0.3 |
| Infinity | 91.6 | 2.1 | 104.7 | 1.9 | 102.9 | 1.2 |

Methods

Particle Size

Particle size was measured by first dispersing the sample in 0.1% HPC, 0.01N HCl and sonicating for 1 minute with a probe sonicator. The sonicated samples were added to the laser light diffractor wet sample unit, filled with 0.1% HPC in 0.01N HCl, stirred for 5 minutes and then the sample was measured.

Dissolution Rate

The dissolution of selected powder intermediate formulations was tested using the USP Apparatus II, with 900 mL of 50 mM pH 5.8 media at 37° C. and a 50 rpm paddle speed. The powder was added to the top of the media-filled vessels, and samples were assayed by HPLC to obtain the results.

Example 2: Co-Jet Milling Provides Improved Dissolution for Ibuprofen

The jet milling results suggested that it could provide a means for preparing a dosage form containing a high drug load of both ibuprofen and acetaminophen. Jet milling was further investigated by manufacturing a powder formulation using two different jet milling methods, both of which employed the formula in Table 4. In the first process, ibuprofen was jet milled alone and then blended with the acetaminophen, SLS and hydroxypropyl cellulose. In the second process, all four ingredients were blended and then co-jet milled.

TABLE 4

Formulation for comparisons of jet milling and co-jet milling Formula

| Ingredient | % w/w |
|---|---|
| Ibuprofen | 22% |
| Acetaminophen (APAP) | 74% |
| Sodium Lauryl Sulfate (SLS) | 2% |
| Hydroxypropyl cellulose (HPC) | 2% |
| Total | 100% |

The particle size of jet-milled ibuprofen, whether jet-milled alone or co-jet milled with acetpminophen, SLS and HPC was similar, as shown in Table 5.

TABLE 5

Particle size of jet milled and co-jet milled ibuprofen

| | Dv10 (µm) | Dv50 (µm) | Dv90 (µm) |
|---|---|---|---|
| Jet milled ibuprofen | 1.46 | 2.53 | 3.97 |
| Co-Jet-milled ibuprofen, APAP, SLS, HPC | 1.31 | 2.51 | 4.32 |

It was unexpectedly found that when ibuprofen was size reduced by co-jet milling with acetaminophen, SLS and hydroxypropyl cellulose, the dissolution rate was improved relative to ibuprofen that was size reduced by jet milling in the absence of acetaminophen, SLS and hydroxypropyl cellulose despite the fact that the two methods yielded similarly-sized ibuprofen particles. Table 6 presents data on the dissolution rate of 1) jet-milled ibuprofen that was blended with acetaminophen, SLS and hydroxypropyl cellulose after jet milling; and 2) ibuprofen that was co-jet milled with acetaminophen, SLS and hydroxypropyl cellulose.

It can be seen from the dissolution data in Table 6 that the ibuprofen co-jet milled with acetaminophen, SLS and HPC fully dissolved within 2 minutes whereas the ibuprofen milled in the absence of acetaminophen, SLS and HPC took 10 minutes to exceed 85% dissolved. Hence, the presence of acetaminophen, SLS and HPC in the milling improve the dissolution rate of similarly sized ibuprofen.

TABLE 6

Dissolution data for jet milled and co-jet milled ibuprofen

| | Jet-milled ibuprofen subsequently blended with acetaminophen, SLS, hydroxypropyl cellulose | | Ibuprofen co-jet milled with acetaminophen, SLS, and hydroxypropyl cellulose | |
|---|---|---|---|---|
| Time (min) | Avg % ibuprofen dissolved | % RSD (n = 3) | Avg % ibuprofen dissolved | % RSD (n = 3) |
| 2 | 80.0 | 13.9 | 100.0 | 0.6 |
| 5 | 83.1 | 14.3 | 104.5 | 0.4 |
| 10 | 86.8 | 11.4 | 104.6 | 0.6 |
| 15 | 89.6 | 9.6 | 104.8 | 0.7 |
| 30 | 94.2 | 6.5 | 104.8 | 0.7 |
| 45 | 98.4 | 3.8 | 104.6 | 0.6 |

The particle size and dissolution rate methods were the same as those described in Example 1.

Example 3: Preparation of Examples of Rapid Maxigesic 325 Tablets and Rapid Maxigesic 500 Tablets Acetaminophen (75.41% w/w), ibuprofen (22.62% w/w) and sodium lauryl sulfate (1.97% w/w) were blended together, and the blend was milled using a spiral jet mill to achieve a target bulk particle size of $Dv50<4.5$ micron and $Dv90<14$ microns. The milled blend ("Drug Product Intermediate" or DPI) was then blended with excipients and wet granulated using a high shear mixer and fluid bed dryer. The granulation was screened/milled, blended with lubricant and compressed into tablets. The tablets were then film coated. Table 7 shows the formulation of the milled intermediate, and Tables 8 and 9 show the tablet formulations.

TABLE 7

Example of Drug Product Intermediate for Rapid Maxigesic 325 and 500

| Ingredient | % w/w |
|---|---|
| Acetaminophen, USP | 75.41 |
| Ibuprofen, USP | 22.62 |
| Sodium Lauryl Sulfate, USP | 1.97 |
| | 100.00 |

TABLE 8

Example of Tablet Formulation for Rapid Maxigesic (325)
Rapid Maxigesic 325 Tablet
(325 mg acetaminophen, 97.5 mg ibuprofen)

| Intragranular | % w/w | mg/tablet |
|---|---|---|
| Drug Product Intermediate 75.41% APAP 22.62% Ibuprofen 1.97% SLS | 74.75 | 431.0 |
| Microcrystalline Cellulose (Avicel PH101) | 9.00 | 51.9 |
| Lactose Monohydrate (Lactose 310) | 11.74 | 67.7 |
| Croscarmellose Sodium (Ac-di-Sol) | 2.00 | 11.5 |
| Povidone (K30) | 2.00 | 11.5 |
| Purified Water extragranular | qs | — |
| Magnesium stearate | 0.50 | 2.9 |
| Total tablet core | 100.00 | 576.6 |
| Film coating | | |
| Opadry II 57U18539, White (hypromellose, titanium dioxide, polydextrose, talc, maltodextrin, medium chain triglycerides) | 2.25 | 13.0 |
| Total | | 593.8 mg |

TABLE 9

Example of Tablet Formulation for Rapid Maxigesic (500)
Rapid Maxigesic 500 Tablet
(500 mg acetaminophen, 150 mg ibuprofen)

| Intragranular | % w/w | mg/tablet |
|---|---|---|
| Drug Product Intermediate 75.41% APAP 22.62% Ibuprofen 1.97% SLS | 74.75 | 663.0 |
| Microcrystalline Cellulose (Avicel PH101) | 9.00 | 79.8 |
| Lactose Monohydrate (Lactose 310) | 11.74 | 103.8 |
| Croscarmellose Sodium (Ac-di-Sol) | 2.00 | 17.7 |
| Povidone (K30) | 2.00 | 17.7 |
| Purified Water extragranular | qs | |
| Magnesium stearate | 0.50 | 4.4 |
| Total tablet core | 100.00 | 887.0 |
| Film coating | | |
| Opadry II 57U18539, White (hypromellose, titanium dioxide, polydextrose, talc, maltodextrin, medium chain triglycerides) | 2.00 | 17.7 |
| Total | | 904.7 |

Particle Size

Several lots of DPI were analyzed to determine the particle size of ibuprofen within the co-jet milled intermediate. All testing was conducted using laser light diffraction. To measure ibuprofen particle size the DPI was dispersed in an aqueous media in which the acetaminophen and SLS are soluble (0.1% HPC in 0.01N HCl), leaving only the poorly soluble ibuprofen suspended for particle size testing. Specifically, the powder was directly added to the sample chamber and stirred for 5 minutes, then the sample measurement was taken. The results of this analysis are in Table 10.

TABLE 10

Particle size data for Rapid Maxigesic DPI

| | Ibuprofen | | |
|---|---|---|---|
| Lot | $D_{10}$ (µm) | $D_{50}$ (µm) | $D_{90}$ (µm) |
| 10-1 | 2.15 | 4.19 | 8.22 |
| 10-2 | 1.67 | 3.03 | 5.48 |
| 10-3 | 1.72 | 3.45 | 6.95 |
| 10-4 | 2.55 | 5.26 | 10.6 |
| 10-5 | 2.35 | 4.84 | 9.97 |
| 10-6 | 2.97 | 6.89 | 14.3 |
| 10-7 | 3.15 | 7.30 | 14.7 |

Dissolution Rate

The dissolution of selected tablet formulations was tested using the USP Apparatus II, with 900 mL of 50 mM pH 5.8 media at 37° C. and a 50 rpm paddle speed. One tablet was added to each media-filled vessel, and samples were assayed by HPLC to obtain the results.

The film coating is present to aid in swallowing, mask taste, and for pharmaceutical elegance. Film coatings typically take a few minutes to dissolve, creating a small lag time in the dissolution. To facilitate comparison, both film coated and uncoated core tablets were studied. The tablets in these lots were prepared using the DPIs in Table 11. The results of this analysis are depicted in Table 11.

TABLE 11

Dissolution of Rapid Maxigesic 325
Ibuprofen dissolution in pH 5.8 buffer

| time | LOT 12-A (coated) avg % | % RSD n = 6 | LOT 12-B (coated) avg % | % RSD n = 6 | LOT 12-C (uncoated) avg % | % RSD n = 6 | LOT 12-D (uncoated) avg % | % RSD n = 6 | LOT 12-E (uncoated) avg % | % RSD n = 6 |
|---|---|---|---|---|---|---|---|---|---|---|
| 5 | 54 | 18.1 | 28 | 28.2 | 47 | 10.2 | 50 | 9.4 | 63 | 7.6 |
| 10 | 94 | 5.4 | 78 | 7.8 | 80 | 4.6 | 87 | 2.2 | 95 | 2.3 |
| 15 | 98 | 2.4 | 93 | 2.5 | 94 | 0.3 | 96 | 0.9 | 101 | 0.9 |
| 20 | 100 | 1.6 | 96 | 1.4 | 95 | 1 | 98 | 1.6 | 102 | 0.7 |
| 30 | 100 | 1.6 | 97 | 0.8 | 96 | 0.3 | 97 | 1.6 | 102 | 0.8 |
| 45 | 101 | 0.8 | 98 | 0.5 | 96 | 0.6 | 97 | 1.9 | 102 | 0.6 |

In a separate study, the dissolution rate of ibuprofen in two different lots of Rapid Maxigesic 325 tablets (prepared as described above) was compared to that of Maxigesic Tablets 325 (measured in pH 5.8 phosphate buffer, as described above). The results are presented in Table 12. A similar comparison was performed for Rapid Maxigesic 500 and Maxigesic 500 tablets. The results are shown in Table 13.

TABLE 12

Dissolution of Rapid Maxigesic 325 and Maxigesic 325
Tablets in pH 5.8 Phosphate Buffer

| Time (min) | Rapid Maxigesic 325 (Lot X) % Ibuprofen dissolved | % RSD (n = 12) | Rapid Maxigesic 325 (Lot Y) % Ibuprofen dissolved | % RSD (n = 12) | Maxigesic 325 % Ibuprofen dissolved | % RSD (n = 12) |
|---|---|---|---|---|---|---|
| 5 | 57 | 13.7 | 81 | 8.1 | 42 | 12.2 |
| 10 | 91 | 3.0 | 95 | 1.6 | 59 | 5.6 |
| 15 | 95 | 2.9 | 98 | 1.7 | 69 | 5.5 |
| 20 | 97 | 1.3 | 99 | 1.3 | 77 | 4.3 |
| 30 | 98 | 1.2 | 100 | 1.0 | 84 | 4.5 |
| 45 | 99 | 1.0 | 100 | 1.0 | 89 | 3.1 |
| F2 | 34 | | 28 | | Reference | |

TABLE 13

Dissolution of Maxigesic 500 and Rapid Maxigesic
500 Tablets in pH 5.8 Phosphate Buffer

| Time (min) | Rapid Maxigesic 500 (Lot Z) % Ibuprofen dissolved | % RSD (n = 6) | Maxigesic 500 % Ibuprofen dissolved | % RSD (n = 6) |
|---|---|---|---|---|
| 5 | 80.8 | 8.9 | 42.6 | 14.5 |
| 10 | 95.6 | 3.1 | 65.2 | 11.3 |
| 15 | 98.1 | 2.2 | 72.2 | 6.9 |
| 20 | 99.7 | 1.5 | 77.1 | 3.3 |
| 30 | 100.8 | 1.3 | 83.1 | 2.7 |
| 45 | 100.8 | 1.5 | 88.1 | 2.2 |
| F2 | 34 | | Reference | |

From the results describe above, it can be seen that it is possible to prepare solid oral dosages forms with greatly improved dissolution of ibuprofen, despite the ibuprofen having a median particle size (on a volume average basis) that is larger than 1 micron.

Example 4: Pharmacokinetic Analysis of Rapid Maxigesic 325 in Comparison to Maxigesic 325

A clinical study was undertaken in which the Cmax for ibuprofen and the Cmax for acetaminophen was assessed in both the fasting and fed states.

This data was tested using individual 90% CI, two-tailed, unpaired t-tests. Comparisons were made between Maxigesic Rapid 325 and Maxigesic 325 in either fed or fasting conditions. This allows for a significant difference to be detected at 10% or $P \leq 0.1$. The study protocol already used a 90% Cl to calculate the mean differences in the mean log transformed data of acetaminophen and ibuprofen.

For acetaminophen in the fasting state there was no statistically significant difference in Cmax between the formulations Table 13.

TABLE 13

Acetaminophen fasting Cmax Maxigesic
325 and Rapid Maxigesic 325

| | |
|---|---|
| Difference between means | −459.1 ± 1665 |
| 90% confidence interval | −3243 to 2325 |
| Percentage difference between means | −2.99% |

For ibuprofen in the fasting state there was a statistically significant difference in Cmax between the formulations (Table 14)

TABLE 14

Ibuprofen fasting Cmax Maxigesic 325 and Rapid Maxigesic 325

| | |
|---|---|
| Difference between means | −2727 ± 1443 |
| 90% confidence interval | −5138 to −315.6 |
| Percentage difference between means | 11.93% |

This is an important advantage of the present dosage forms since dosing on an empty stomach is advised in order to achieve fast onset of pain relief.

For acetaminophen in the fed state there was no statistically significant difference in Cmax between the formulations (Table 15).

TABLE 15

Acetaminophen fed Cmax Maxigesic 325 and Rapid Maxigesic 325

| | |
|---|---|
| Difference between means | −813.1 ± 996 |
| 90% confidence interval | −2478 to 851.7 |
| Percentage difference between means | 7.82% |

For ibuprofen in the fed state there was no statistically significant difference in Cmax between the formulations, although a significant increase was again observed (Table 16)

TABLE 16

Ibuprofen fed Cmax Maxigesic 325 and Rapid Maxigesic 325

| | |
|---|---|
| Difference between means | 2344 ± 1362 |
| 90% confidence interval | 67.02 to 4622 |
| Percentage difference between means | 12.68% |

To summarize, in both studies, fed and fasting, the Cmax of ibuprofen in Maxigesic Rapid (325) was significantly higher than Maxigesic (325). The 90% confidence intervals did not overlap with 0 which shows a significant difference between the means. There was a difference of >11% between the ibuprofen means, consistent with the Maxigesic Rapid formulation delivering higher Cmax drug concentrations of ibuprofen.

Example 5: Phamacokinetic Analysis of Maxigesic 325

A pharmacokinetic analysis of the Maxigesic 325 formulation described above was conducted under fed and fasting conditions. The results of this study are presented in Tables 17-20.

TABLE 17

Ibuprofen PK Values for Maxigesic Rapid 325 in Fasting condition

| Pharmacokinetic Parameter | (N = 30) |
|---|---|
| $C_{max}$ (ng/ml) | 25579.823 ± 5996.24 |
| $AUC_{0 \to t}$ (ng · h/ml) | 91888.7 ± 24015.73 |
| $AUC_{0 \to \infty}$ (ng · h/ml) | 95621.9 ± 28252.68 |
| $t_{max}$ (h) * | 1.25 (0.25-3.00) |
| $K_{el}$ (l/h) | 0.3076 ± 0.06 |
| $t_{1/2el}$ (h) | 2.35 ± 0.57 |
| $AUC_{0 \to t}/AUC_{0 \to \infty}\%$ | 96.82 ± 3.22 |

TABLE 18

Ibuprofen PK Values for Maxigesic Rapid 325 in Fed Condition

| Pharmacokinetic Parameter | (N = 30) |
|---|---|
| $C_{max}$ (ng/ml) | 20834.673 ± 5506.39 |
| $AUC_{0 \to t}$ (ng · h/ml) | 71286.1 ± 16546.13 |
| $AUC_{0 \to \infty}$ (ng · h/ml) | 73449.6 ± 17660.44 |
| $t_{max}$ (h) * | 1.25 (0.75-6.00) |
| $K_{el}$ (l/h) | 0.3222 ± 0.05 |
| $t_{1/2el}$ (h) | 2.19 ± 0.31 |
| $AUC_{0 \to t}/AUC_{0 \to \infty}\%$ | 97.25 ± 1.42 |

TABLE 19

Acetaminophen PK Values for Maxigesic Rapid 325 in Fasting Condition

| Pharmacokinetic Parameter | ®(N = 29) |
|---|---|
| $C_{max}$ (ng/ml) | 14877.280 ± 5969.64 |
| $AUC_{0 \to t}$ (ng · h/ml) | 44637.6 ± 11784.46 |
| $AUC_{0 \to \infty}$ (ng · h/ml) | 47437.2 ± 13053.06 |
| $t_{max}$ (h) * | 0.75 (0.25-2.00) |
| $K_{el}$ (l/h) | 0.2233 ± 0.05 |
| $t_{1/2el}$ (h) | 3.25 ± 0.75 |
| $AUC_{0 \to t}/AUC_{0 \to \infty}\%$ | 94.43 ± 2.54 |

TABLE 20

Acetaminophen PK Values for Maxigesic Rapid 325 in Fed Condition

| Pharmacokinetic Parameter | (N = 30) |
|---|---|
| $C_{max}$ (ng/ml) | 11214.182 ± 4084.46 |
| $AUC_{0 \to t}$ (ng · h/ml) | 39826.6 ± 11211.91 |
| $AUC_{0 \to \infty}$ (ng · h/ml) | 42381.0 ± 12086.45 |
| $t_{max}$ (h) * | 1.25 (0.50-6.00) |
| $K_{el}$ (l/h) | 0.2303 ± 0.03 |
| $t_{1/2el}$ (h) | 3.05 ± 0.37 |
| $AUC_{0 \to t}/AUC_{0 \to \infty}\%$ | 94.16 ± 2.30 |

OTHER EMBODIMENTS

All publications, patents, and patent applications mentioned in this specification are incorporated herein by reference to the same extent as if each independent publication or patent application was specifically and individually indicated to be incorporated by reference.

While the disclosure has been described in connection with specific embodiments thereof, it will be understood that it is capable of further modifications and this application is intended to cover any variations, uses, or adaptations of the disclosure following, in general, the principles of the disclosure and including such departures from the disclosure that come within known or customary practice within the art to which the disclosure pertains and may be applied to the essential features hereinbefore set forth, and follows in the scope of the claims.

Other embodiments are within the claims.

What is claimed is:

1. A tablet comprising 325 mg of acetaminophen and 97.5 mg of ibuprofen or 500 mg of acetaminophen and 150 mg of ibuprofen, wherein the ibuprofen has a [D50] between 2 and 8 μm and the [D90] to [D50] ratio is between 4:1 and 1.5:1, wherein the ibuprofen is prepared by a method comprising jet milling ibuprofen together with acetaminophen and a surfactant.

2. The tablet of claim 1, wherein the ibuprofen has a [D10] between 1 and 3 µm.

3. The tablet of claim 1, wherein the ibuprofen has a [D90] between 3 and 16 µm.

4. The tablet of claim 1, wherein the ibuprofen has a [D50] between 2 and 8 µm, a [D10] between 1 and 3 µm and a [D90] between 4 and 16 µm.

5. The tablet of claim 1 wherein the dissolution rate of ibuprofen in the solid oral dosage form is such that, when tested using USP Apparatus II (paddles) set to rotation speed of 50 rpm in 900 mL of 50 mM pH 5.8 phosphate buffer at 37° C., wherein 80% or more of the ibuprofen dissolves in 15 minutes or less.

6. The tablet of claim 5, wherein at least 85% to 95% of the ibuprofen dissolves in 15 minutes or less.

7. The tablet of claim 5, wherein at least 95% to 100% of the ibuprofen dissolves in 10 minutes or less.

8. The tablet of claim 1, wherein the tablet is coated.

9. The tablet of claim 1, wherein the [D90] to [D50] ratio is between 3:1 and 1.5:1.

10. The tablet of claim 1, wherein the [D50] to [D10] ratio is between 4:1 and 1.5:1.

11. The tablet of claim 1, wherein the [D50] to [D10] ratio is between 3:1 and 1.5:1.

12. The tablet of claim 1, wherein the tablet is a coated tablet.

13. The tablet of claim 1, prepared by a process comprising jet milling a composition comprising 21-23% wt/wt ibuprofen and 73-75% wt/wt acetaminophen.

14. The tablet of claim 1, wherein the surfactant is sodium lauryl sulfate.

15. The tablet of claim 5, wherein 85% to 95% of the ibuprofen dissolves in 15 minutes.

16. The tablet of claim 5, wherein 95% to 100% of the ibuprofen dissolves in 10 minutes.

17. A method for treating pain comprising administering a dose of 1, 2 or 3 units of the tablet of claim 1 comprising 325 mg of acetaminophen and 97.5 mg of ibuprofen.

18. The method of claim 17, wherein the administration is 1, 2, 3 or 4 times daily.

19. A method for treating pain comprising administering a dose of 1 or 2 units of the solid oral dosage form of claim 1 comprising 500 mg of acetaminophen and 150 mg of ibuprofen.

20. The method of claim 19, wherein the administration is 1, 2, 3 or 4 times daily.

21. The method of claim 17, wherein the pain is mild to moderate acute pain.

* * * * *